United States Patent [19]
Koizumi

[11] Patent Number: 5,329,321
[45] Date of Patent: Jul. 12, 1994

[54] INTRAOCULAR LENGTH MEASURING INSTRUMENT WITH ROTARY OPTICAL PATH LENGTH VARIATOR

[75] Inventor: Hiroshi Koizumi, Tokyo, Japan

[73] Assignee: Kabushiki Kaisha TOPCON, Tokyo, Japan

[21] Appl. No.: 33,549

[22] Filed: Mar. 18, 1993

[30] Foreign Application Priority Data

Mar. 19, 1992 [JP] Japan .................. 4-063048

[51] Int. Cl.$^5$ .................................................. A61B 3/10
[52] U.S. Cl. .................................. 351/205; 351/211; 351/221
[58] Field of Search .............. 351/205, 211, 204, 206, 351/207, 208, 221

[56] References Cited

U.S. PATENT DOCUMENTS

| | | | |
|---|---|---|---|
| 4,796,989 | 1/1989 | Fukuma et al. | 351/205 X |
| 5,042,938 | 8/1991 | Shimozono | 351/211 X |
| 5,141,302 | 8/1992 | Arai et al. | 351/205 |

Primary Examiner—William L. Sikes
Assistant Examiner—David R. Parsons
Attorney, Agent, or Firm—Finnegan, Henderson, Farabow, Garrett & Dunner

[57] ABSTRACT

An intraocular length measuring instrument in which a measuring optical path is formed via an eye to be tested, and a reference optical path having a variable optical path length is formed within the instrument, light via the measuring object path and reflected by an intraocular object to be measured and light passed through the reference optical path being caused to be interfered with each other, the optical path length of the reference optical path being varied to form interference fringes, the intraocular length being found based on the reference optical path length where the interference fringes are formed, wherein the intraocular length measuring instrument further includes: a rotatable optical path length variable member for varying the optical path length of the reference optical path in accordance with an angle of rotation; and a rotary device for rotating the optical path length variable member to vary the optical path length of the reference optical path sequentially.

10 Claims, 10 Drawing Sheets

INTRAOCULAR LENGTH MEASURING INSTRUMENT WITH ROTARY OPTICAL PATH LENGTH VARIATOR

BACKGROUND OF THE INVENTION

1. Field of the Invention

This invention relates to an intraocular length measuring instrument, in which a beam of light is split into two beams of light, one beam of light is guided to an optical path length variable member disposed at a reference optical path as a reference beam of light and adapted to vary an optical path length of the reference optical path, the other beam of light is guided to an intraocular object to be measured via a measuring optical path as a measuring beam of light, and the reference reflection light from the optical path length variable member and a measuring reflection light from the intraocular object to be measured are caused to be interfered with each other to obtain an interference signal, thereby obtaining a position of the intraocular object. As a result, obtaining the intraocular length.

2. Brief Description of the Prior Art

As a typical example of an intraocular length measuring instrument, there is heretofore known one disclosed in U.S. Pat. No. 5,141,302. This instrument includes a measuring optical path formed via an eye to be tested, and a reference optical path formed within the instrument, light reflected by an intraocular object to be measured after being passed through the measuring optical path and light passed through the reference optical path being caused to be interfered with each other, a reference mirror disposed at the reference optical path being moved to vary the optical path length of the reference optical path, interference fringes being generated by the above interference. Then, a position of the intraocular object to be measured is found with reference to the optical path length of the reference optical path where the interference fringes are generated. A position of a cornea is found by other optical means.

However, in this instrument, since a movement of the reference mirror is a reciprocal linear motion, it is difficult to reciprocate the reference mirror at a high speed repeatedly. Furthermore, the speed of its movement in a whole stroke is impossible to be kept constant. This being the case, there encounter the following problems.

(1) Since it is difficult to reciprocate the reference mirror at high speed repeatedly, a repeated generation of interference fringes are difficult to obtain in a position where the optical path length of the measuring optical system is equal to the optical path length of the reference optical system. Consequently, during the alignment of the instrument and the correction of the refractive error with respect to the eye to be tested, since the alignment and the correction of the refractive error cannot be set to an optimum position while detecting the amplitude of light and darkness of the interference fringes by a photosensor, it is necessary to confirm the alignment and the correction of the refractive error first and then, the interference fringes are observed while moving the reference mirror.

However, in this method, even if the alignment and the correction of the refractive error are once set to the optimum position, it is no way to detect an actual generation of the interference fringes until the reference mirror is moved. Furthermore, there is a possibility that the alignment is displaced when the reference mirror moves to the position where the interference fringes are generated. Particularly, in the case where the eye to be tested is difficult to be measured because the eye is suffered from, for example, cataract, there are many cases that the interference fringes are not obtained. As a consequence, the probability of measurement is lowered.

(2) The frequency of a repetition of light and darkness caused by movement of the interference fringes observed by the photosensor is determined ($2 \times$(moving speed)/(wavelength)) from the wavelength of a light source and a moving speed (variation speed of the optical pathlength of the reference optical system) of the reference mirror. Therefore, if the moving speed of the reference mirror is fluctuated during a stroke thereof, the frequency of light and darkness caused by movement of the interference fringes to be observed is also varied. This makes it necessary to design the band width of the frequency characteristic of a light receiving circuit wide. However, if the band width of the frequency characteristic is designed wide, it becomes difficult to separate a noise component. In other words, it is difficult to realize a high signal to noise ratio (S/N). As a result, it is frequently unable to measure such an intraocular object to be tested as the eye suffered from cataract where losses in an amount of light reflected from the fundus of the eye to be tested are great and the signal to noise ratio (S/N) is bad.

The present invention has been accomplished in view of the above problems. It is therefore an object of the present invention to provide an intraocular length measuring instrument, in which the optical path length of a reference optical path can be converted at a high speed repeatedly.

SUMMARY OF THE INVENTION

According to the present invention, there is provided, in order to achieve the above object, an intraocular length measuring instrument including a light source having a short coherent length, a beam splitter for forming a measuring optical path via the interior of an eye to be tested and a reference optical path within the instrument, and guiding a beam of light from the light source to both the measuring optical path and the reference optical path, a first light receiving portion for causing light reflected by an intraocular object to be measured after passing through the measuring optical path to interfere with light coming through the reference optical path, and then receiving a resultant interference light, an intraocular object position measuring portion for finding an optical path difference from the reference optical path and the measuring optical path which is according as a peak position of a signal coming from said first light receiving portion and said optical path length of the refrence optical path, a light irradiating optical system for irradiating a light beam to the cornea of the eye to be tested, a light receiving optical system for introducing a reflected light from the cornea to a second light receiving portion and a corneal position measuring portion for finding a position of the cornea from an output of the second light receiving portion. The intraocular length measuring instrument further includes a rotatable optical path length variable member for varying the optical path length of the reference optical path in accordance with an angle of rotation and a rotary means for rotating the optical path length variable member to vary the optical path length of the reference optical path sequentially.

According to another aspect of the present invention, there is provided an intraocular length measuring instrument in which a beam of light is split into two beams of light, one of the beams of light is guided, as a reference beam of light, to an optical path length variable optical member disposed at a reference optical path and adapted to vary an optical path length of the reference optical path, and the other is guided, as a measuring beam of light, to an intraocular object to be measured, a reference reflection light from the optical path length variable optical member and a measuring reflection light from the intraocular object to be measured being interfered with each other to obtain an interference signal, thereby finding a position of the intraocular object to be measured, the improvement being characterized in that the optical path length variable optical member comprises a rotary optical member and a stationary mirror, a rotary axis of the rotary optical member being in parallel or vertical to an optical axis of the reference optical path.

With the above constructions of the present invention, the optical path length of the reference optical path is varied in accordance with the rotation of the rotary optical member. Therefore, the interference fringes can be generated at a high speed repeatedly. Since the alignment and the correction of the refractive error can be set or adjusted to the optimum position while observing the interference fringes, the measuring time can be shortened. Further, also in the case of the eye suffering from cataract, since it is known by means of the rotation of the rotary optical member (optical path length variable member) whether or not the interference fringes can be obtained, an undue or wasteful measurement can be avoided. Therefore, the probability of measurement can be increased. Furthermore, the optical path length of the reference optical path can be varied at an equal speed repeatedly. By doing this, the frequency of light and darkness caused by the movement of the interference fringes to be measured can be maintained constant. As a result, measuring errors caused by the affection of noises, etc. can be decreased. In other words, it becomes possible to measure even the eye suffering from cataract where the amount of light reflecting from the eye fundus is small. In addition, since the alignment of the instrument and the correction of the refractive error can be effected with respect to the eye to be tested while observing the amplitude of the interference fringes, it is no more required to provide additional means for confirming the alignment and the correction of the refractive error.

DETAILED DESCRIPTION OF THE EMBODIMENT

Figure 1:
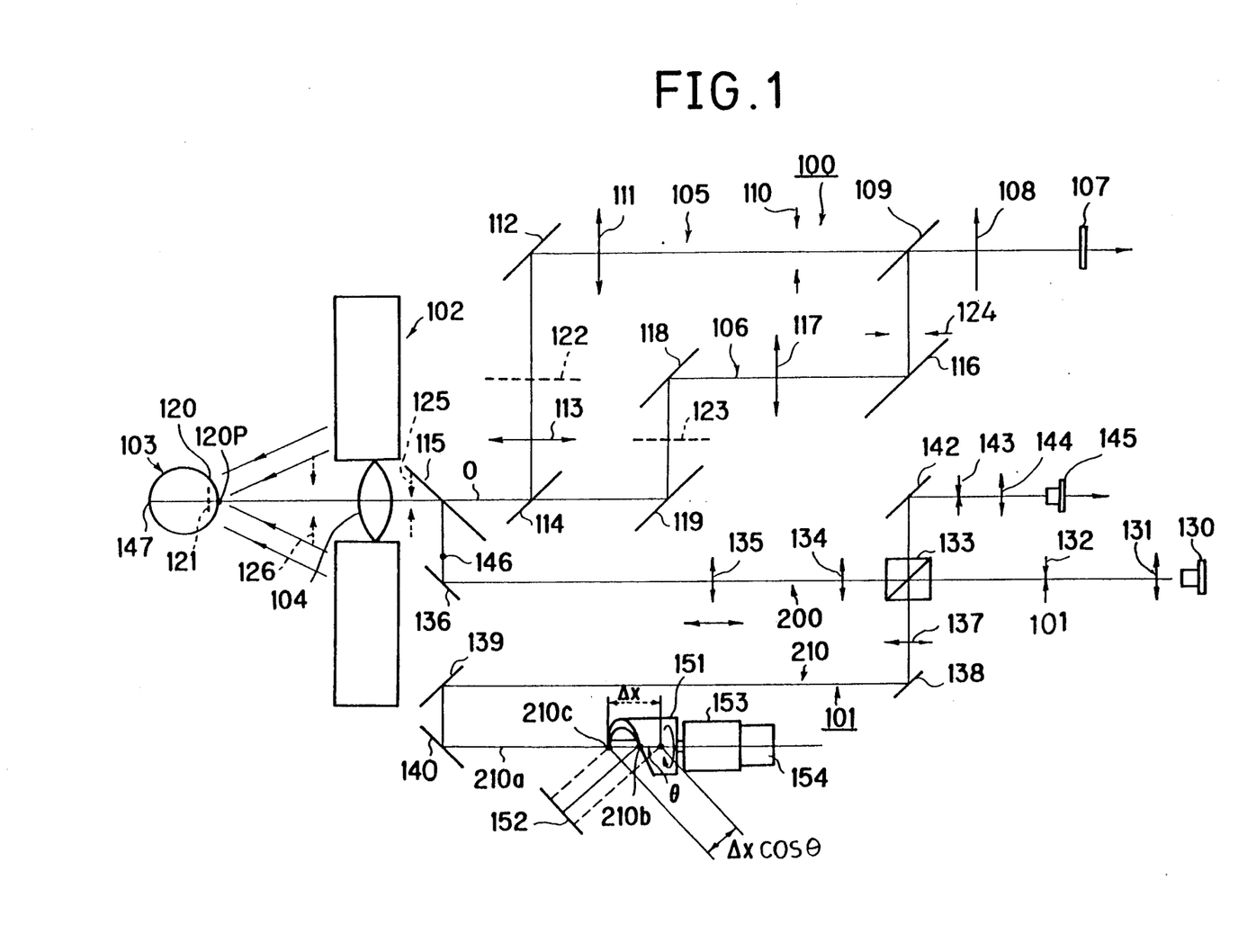
FIG. 1 is a view showing an arrangment of optical system of an ophthalmologic instrument according to the present invention.

In FIG. 1, the numeral 100 denotes a cornea distance measuring system, 101 an interference optical system, 102 a ring-shaped light source projecting portion acting as a light irradiating optical system for irradiating light beam to the cornea of an eye to be tested, 103 the eye to be tested, and 104 an objective lens. The cornea distance measuring system 100 has a first optical path 105, and a second optical path 106.

The first optical path 105 generally comprises a two-dimensional image sensor 107 acting as a second light receiving portion, an imaging lens 108, a half mirror 109, a diaphragm 110, a lens 111, a total reflecting mirror 112, a lens 113, a half mirror 114, a dichroic mirror 115, and an objective lens 104. The second optical path 106 generally comprises a half mirror 116, a lens 117, total reflection mirrors 118, 119, and a diaphragm 124.

The ring-shaped light source projecting portion 102 comprises a ring-shaped light source and a pattern plate (not shown). In this embodiment, although an illumination light, which is parallel in rays of light in meridional section, is projected to the eye, a radiating illumination light may be projected to the eye. When this illumination light is irradiated toward the eye 103, a ring-shaped virtual image 121 is formed on a cornea 120 of the eye 103. In this embodiment, the wavelength of the illumination light of the ring-shaped light projecting portion 102 is 900 nm to 1000 nm. The dichroic mirror 115 has a role for transmitting the illumination light and reflecting a wavelength of a near infrared light.

A reflected light by the cornea 120 is guided to the half mirror 114 through the objective lens 104 and dichroic mirror 115 and bifurcated to the first and second optical paths 105 and 106. The reflected light guided to the first optical path 105 is once imaged as a ring-shaped air image 122 through the lens 113 and then imaged as a ring image $i_2$ (see FIG. 2) on the two-dimensional image sensor 107 via the total reflection mirror 112, lens 111, diaphragm 110, half mirror 109 and imaging lens 108. The imaging power of this ring image $i_2$ is 0.5 times in this embodiment.

Figure 2:
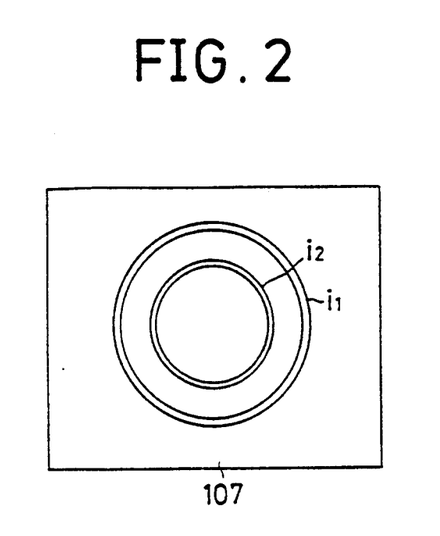
FIG. 2 is a view showing a ring image formed on a two-dimensional image sensor shown in FIG. 1.

The reflected light guided to the second optical path 106 is reflected by the total reflection mirror 119, then once imaged as an aerial image 123 through the objective lens 104 and then imaged on the two-dimensional image sensor 107 as a ring image $i_1$ through the total reflection mirror 118, lens 117, half mirror 116, diaphragm 124, half mirror 109, and imaging lens 108. The imaging power of this ring image $i_1$ is set to be larger than the imaging power of the ring image $i_2$.

The diaphragm 110 has a role of acting as a second diaphragm and is relayed to the neighborhood of the focusing position behind the objective lens 104 by the lens 113. The first optical system 100 is generally telecentric toward the object side. The diaphragm 124 has a role for acting as a first diaphragm and is relayed to the forward of the testing eye 103 by the lens 117. Here, a conjugate image (real image) 126 is formed in a position 25 mm to 50 mm away forwardly from the eye.

Figure 3:
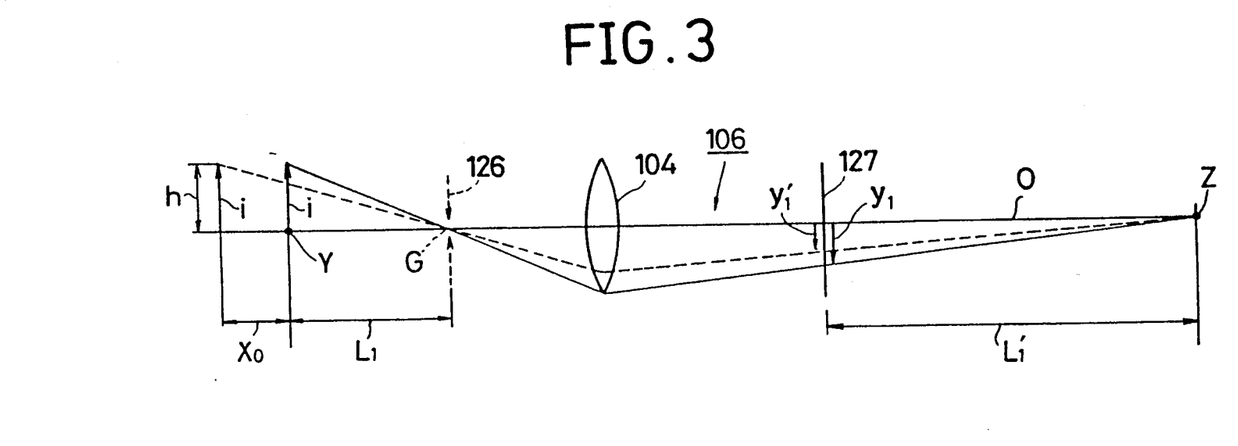
FIG. 3 is an explanatory view for schematically explaining the operation of an cornea distance measuring optical system shown in FIG. 1.
Figure 4:
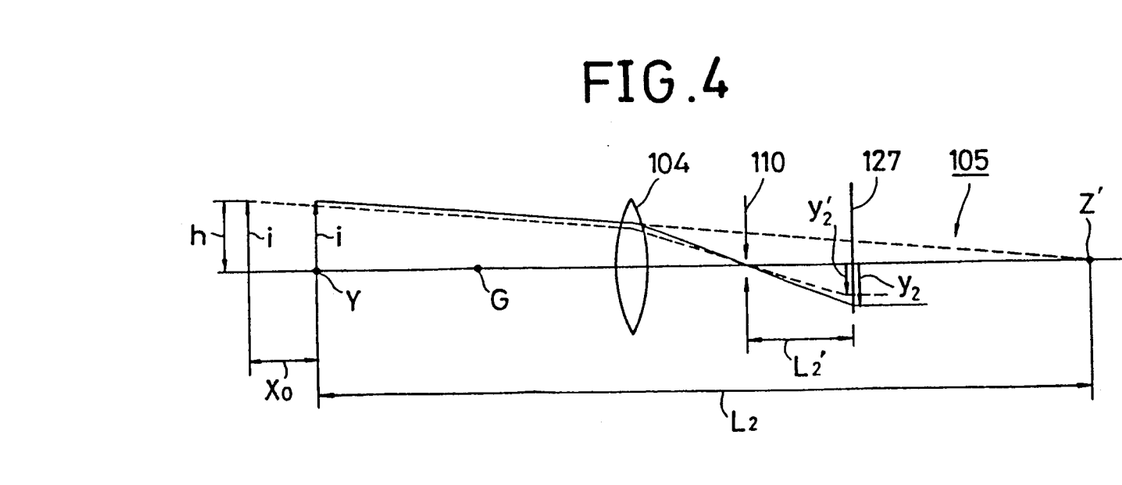
FIG. 4 is likewise an explanatory view for schematically explaining the operation of an cornea distance measuring optical system shown in FIG. 1.

This embodiment will be described in more detail with reference to FIGS. 3 and 4 which schematically show a relation between the objective lens 104 and the diaphragms 110, 124.

In this embodiment, an origin G is set to one point on an optical axis O where the conjugate image 126 of the diaphragm 124 is formed, and a reference position Y is set to a position away in the direction of the optical axis O from the origin G by a distance $L_1$. The location of this reference position Y is deliberately determined so that the ring images $i_1$ and $i_2$ are not defocused. It may be good that the ring imagees $i_1$ and $i_2$ are propary sharp. An object having a height h (this height is equal to the radius of the ring image i) is placed at this reference position Y. The height of an image formed on an observing plane 127 (position where the two-dimensional image sensor 107 is located) by the second optical path 106 at this time is represented by $y_1$ and the height of another image formed on the observing plane 127 by the first optical path 105 is represented by $y_2$.

Then, this known object is moved by a distance $X_0$ and the heights of the images in these new positions are represented by $y_1'$ and $y_2'$, respectively. Further, a distance from the observing plane 127 to a point Z is represented by $L_1'$, a distance from the reference position Y to a point Z' is represented by $L_2$, and a distance from the diaphragm 110 to the observing plane 127 is represented by $L_2'$. Further more, a magnifying power for relaying the diaphragm 126 to the point Z is represented by $\beta_1$ and a magnifying power for relaying the diaphragm 110 to the point Z' is likewise represented by $\beta_2$.

Then, the following relations can be obtained.

$$h/L_1 = y_1 \cdot \beta_1 / L_1' \tag{1}$$

$$h/(L_1 + X_0) = (y_1' \cdot \beta_1)/L_1' \tag{2}$$

$$h/L_2 = y_2/(\beta_2 \cdot L_2) \tag{3}$$

$$h/(L_2 + X_0) = y_2'/(\beta_2 \cdot L_2') \tag{4}$$

Presuming that the magnifying power $\beta_1$, and the distances $L_1$, $L_1'$ are all constant in the above-mentioned relations (1) and (2), if the following replacement is made, $$K_1 = (\beta_1 \cdot L_1)/L_1'$$

$$K_2 = \beta_1 / L_1'$$

then the relations (1) and (2) are rewritten as follows;

$$h = K_1 \cdot y_1 \tag{5}$$

$$h = K_1 \cdot y_1' + K_2 \cdot y_1' \cdot X_0 \tag{6}$$

Likewise, presuming that the magnifying power $\beta_2$ and the distances $L_2$, $L_2'$ are all constant in the above-mentioned relations (3) and (4), if the following replacement is made, $$K_3 = L_2/(L_2' \cdot \beta_2)$$

$$K_4 = 1/(L_2' \cdot \beta_2)$$

then the relations (3) and (4) are rewritten as follows;

$$h = K_3 \cdot y_2 \tag{7}$$

$$h = K_3 \cdot y_2' + K_4 \cdot y_2' \cdot X_0 \tag{8}$$

Now, the constants $K_1$, $K_2$, $K_3$ and $K_4$ can be determined by actually measuring the height h of the object and the height y of the image.

That is, by rewriting the relations (5) and (6), the following relations can be obtained.

$$K_1 = h/y_1 \tag{9}$$

$$K_2 = (h/y_1) \cdot (y_1 - y_1')/(y_1' \cdot X_0) \tag{10}$$

$$K_3 = h/y_2 \tag{11}$$

$$K_4 = (h/y_2) \cdot (y_2 - y_2')/(y_2' \cdot X_0) \tag{12}$$

Thus, by actually measuring the height h of a known object as well as the height of its image, the contacts $K_1$, $K_2$, $K_3$ and $K_4$ are obtained.

Next, there will be described how the measurement is carried out when the height h of an image and the distance X from the reference position Y are unknown.

In this case, a distance X is substituted for the distance $X_0$ in the above-mentioned relations (2) and (4). Further, $y_1$ and $y_2$ are substituted for $y_1'$ and $y_2'$.

Then, the following relations are obtained.

$$h = K_1 \cdot y_1 + K_2 \cdot y_1 \cdot X \tag{13}$$

$$h = K_3 \cdot y_2 + K_4 \cdot y_2 \cdot X \tag{14}$$

If the above simultaneous equations are simultaneously solved for the distance X and the height h of the object, the following answers can be obtained.

$$X = (K_3 \cdot y_2 - K_1 \cdot y_1)/(K_2 \cdot y_1 - K_4 \cdot y_2) \tag{15}$$

$$\begin{aligned}h &= K_1 \cdot y_1 + K_2 \cdot y_1 \cdot X \\ &= (K_2 \cdot K_3 - K_1 \cdot K_4) y_1 \cdot y_2/(K_2 \cdot y_1 - K_4 \cdot y_2)\end{aligned} \tag{16}$$

Therefore, by measuring the image heights $y_1$ and $y_2$, the distance from the object from the reference position Y can be measured.

Next, the measurements of the radius R of curvature of a cornea and the position of its vertex will be described with reference to FIG. 5.

Figure 5:
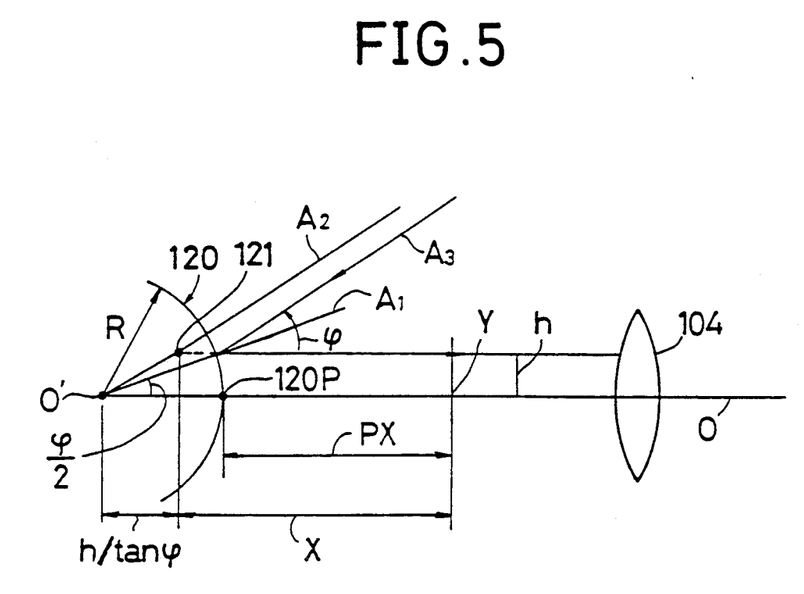
FIG. 5 is an explanatory view for explaining detection of a corneal vertex position.

In FIG. 5, the radius (the long diameter or the short diameter when it resembles an ellipse) of a ring image i is presumed to be the height h of the object. At this time, the object height h is determined by a meridional ray. If the diameter of the ring image is approximately 3 mm, the angle $\phi$ becomes approximately 20°, and the under-listed paraxial calculating equation cannot be used.

$$h = (R \cdot \sin \phi)/2$$

Therefore, if the distance $L_2$ is set to be large enough, the angle $\phi$ is normally held to be constant and one measured by the second optical path 106 passing the diaphragm 124 is used as the object height h, an equation based on the under-listed reflexive law can be used.

$$h = R \cdot \sin(\phi/2) \qquad (17)$$

If the above equation is rewritten, the following equation is obtained.

$$R = h / \sin(\phi/2) \qquad (18)$$

If the position of the corneal vertex is presumed to be a distance $P_x$ as shown in FIG. 5, the following equation can be obtained.

$$P_x = X - (R - h/\tan\phi) \qquad (19)$$

Then, the object height h obtained in accordance with the equation (16) is substituted for the above equation (18) to find R. If R, h and X just obtained from the equation (16) are substituted for the equation (19), the distance $P_x$ from the reference position Y to the corneal vertex is found.

That is, the distance $P_x$ can be found from radii of the ring images $i_1$ and $i_2$ formed on the two-dimensional image sensor 107. This calculation is carried out by an arithmetic unit not shown.

In FIG. 5, O' represents the center of curvature of the cornea. $A_1$ represents a normal line, $A_2$ represents a spherical optical axis when the cornea 120 is regarded as a spherical surface, and $A_3$ represents an incident ray to the cornea 120.

Next, the interference optical system will be described with reference to FIG. 1.

The interference optical system 101 includes a laser diode 130, a lens 131, a pin hole 132, a beam splitter 133, a lens 134, a focusing lens 135, a mirror 136, a lens 137, a mirrors 138, 139 and 140, a rotary mirror 151, a mirror 142, a pin hole 143, a lens 144, and a photosensor 145 having a point aperture.

The laser diode 130 is of a short coherent length. The coherent length is, for example, approximately 0.05 mm to 1 mm. The wavelength is near infrared and has an effect for preventing dazzling. A laser beam emitted from the laser diode 130 is condensed to the pin hole 132 by the lens 131. The pin hole 132 has a role for acting as a secondary point-like source of light. Instead of the laser diode, an LED having a narrow spectral width may be used as a light source.

A laser beam transmitted through the pin hole 132 is split into a light beam proceeding to the lens 134 and another light beam proceeding to the lens 137 by the beam splitter 133. The lens 134 constitutes a measuring optical path 130' together with the lens 135, mirror 136, and dichroic mirror 115. The other lens 137 constitutes a reference optical path 140' together with the mirrors 138, 139 and 140 and rotary mirror 151.

Figure 6:
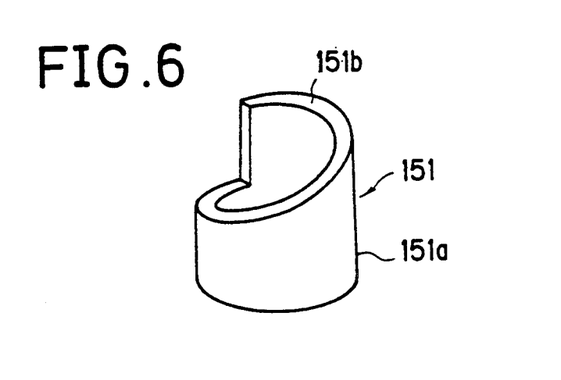
FIG. 6 is a perspective view showing a configuration of a rotary mirror.
Figure 7:
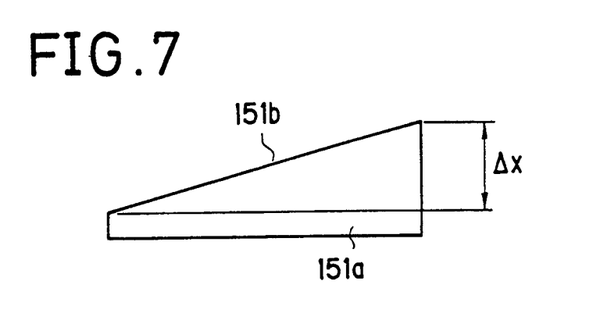
FIG. 7 is an explanatory view showing an inclined condition of a reflecting surface of the rotary mirror.

As shown in FIG. 6, a rotary mirror 151 has a cylindrical body 151a, and a spiral-shaped reflecting surface 151b formed on an end face of the cylindrical body 151a. However, the rotary mirror 151 may have a column configuration. As shown in FIG. 7, the inclination of the reflecting surface 151b becomes a linear line when the cylindrical body 151a is expanded.

Figure 8:
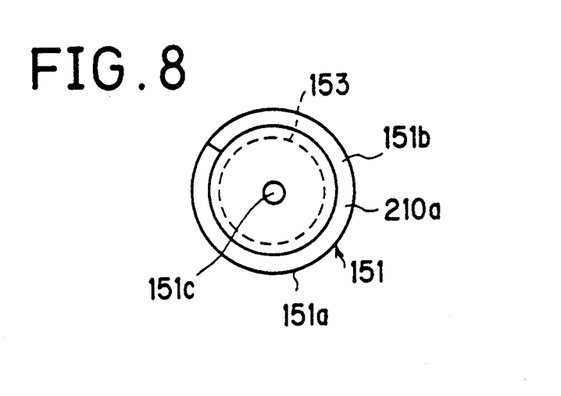
FIG. 8 is a front view of the rotary mirror.

As shown in FIG. 8, in this rotary mirror 151, a rotary axis 151c of the cylindrical body 151a is in parallel to the optical axis 210a. A part of the reflecting surface 151b is disposed in alignment with the optical axis 210a. The cylindrical body 151a is rotated about the rotary axis 151c by a motor (rotary means) 153. Even when the rotary mirror 151 is rotated, its reflecting surface 151b is not deviated from the optical axis 210a. The reflecting surface 151b reflects a reference light made incident from the optical axis 210a towards a stationary mirror 152.

At that time, a reference light of a narrowest-collimated beam is made incident to the reflecting surface 151b. The reflecting surface 151b of the rotary mirror 151 is a curved surface instead of a planar surface. Unless the reference light is a narrow beam, the beam of the reference light is dissipated due to the curved surface of the reflecting surface 151b. As a result, losses of the light amount become significant.

When the rotary mirror 151 is rotated, the reflecting position of the reference light on the reflecting surface 151b is varied along the optical axis 210a. Consequently, the optical path length of the reference optical path 210 is varied. An angle of rotation of the rotary mirror 151 is detected by a rotary encoder 154.

The stationary mirror 152 is disposed perpendicular to the reference light which is made incident to the mirror 152. The stationary mirror 152 is adjusted such that the reference light is reflected in the incident direction of the reference light by the stationary mirror 152. If a phase conjugate mirror is used as the stationary mirror 152, the reference mirror is positively reflected in the incident direction and therefore the stationary mirror is not required to be precisely adjusted.

Each of the lenses 134 and 137 has a role for collimating the laser beam transmitted through the pin hole 132. The laser beam collimated by the lens 134 is caused to form a spot at a focusing position 146 by the focusing lens 135. This focusing position 146 is conjugate with an eye fundus 147 with respect to the objective lens 104 and the eye 103. The laser beam for forming a spot at the focusing position 146 is guided to the testing eye 103 via the mirror 136, dichroic mirror 115, and objective lens 104, and forms a spot on the eye fundus 147. Since the eye fundus 147 and the focusing position 146 are conjugate with each other with respect to the objective lens 104 and the testing eye 103 in this embodiment, even if the optical axis (optical axis 0 of the objective lens) of the measuring instrument is not coaxial with an optical axis of the testing eye 103, a reflected light from the eye fundus 147 forms an image at the focusing position 146.

The pin hole 143 is formed at the focusing position of the lens 134 and is conjugate with the eye fundus 147 to function as a spacial filter. The lens 135 has a role for collimating the reflected light from the eye fundus 147 and such collimated light is relayed to the pin hole 143 via the beam splitter 133 and the mirror 142 by the lens 134. The pin hole 143 becomes conjugate with the pin hole 132 with respect to a reflecting surface of the beam splitter 133. Further, since the pin hole 132 and the spot light on the fundus 147 are conjugate with each other, even if the alignment of the measuring instrument is slightly deviated with respect to the testing eye 103, the reflected light from the eye fundus 147 can transmit through the pin hole 143.

The laser beam collimated by the lens 137 is guided to the rotary mirror 151 by the mirrors 138, 139 and 140.

The reference light guided to the rotary mirror 151 is reflected by the reflecting surface 151b so as to be guided to the stationary mirror 152. The incident light to the stationary mirror 152 is reflected correctly in the incident direction so as to proceed in a reversed direction through the reference optical path 210, and reaches the beam splitter 133. In this beam splitter 133, the reference light and the measuring light reflected from the fundus 147 of the eye to be tested are interfered one upon the other and made incident to the photosensor 145. When the optical path length of the measuring optical path 200 and the optical path length of the reference optical path 210 become generally equal to each other during the variation of the optical path length of the reference optical path 210, the interference fringes are generated on the photosensor 145. The reference fringes are moved as the variation of the optical path length of the reference optical path 210 is progressed.

At that time, the movement of the interference fringes are observed as a repetition of light and darkness in the photosensor 145. The frequency of the repetition of light and darkness is determined from the wavelength of the light source and the speed of variation of the optical path length of the reference optical path 210.

When the rotary mirror 151 is rotated, the reflecting position 210b of the reference light on the reflecting surface 151b is reciprocated on the optical axis of FIG. 1 by a section $\Delta X$. When the reflecting position is varied by $\Delta X$ along the optical axis, a distance between the reflecting position and the stationary mirror 152 is varied by $\Delta X \cos \theta$. As a result, the optical path length of the reference optical path is varied by $\Delta X(1 + \cos \theta)$.

When the rotary mirror 151 is expanded, the angle of rotation of the rotary mirror 151 and the amount of variation of the optical path length are brought to be in linear relation to each other because the gradient of the reflecting surface 151b is linear as shown in FIG. 7. Therefore, when the rotary mirror 151 is rotated at an equal speed, the optical path length of the reference optical path 210 is also varied at a constant speed. As a consequence, the frequency of light and darkness caused by the movement of the interference fringes detected by the photosensor 145 becomes constant, too. This is passed through a band pass filter having a narrow band width and detected as a signal of the high S/N.

The reflecting position 210b on the reflecting surface 151b of the rotary mirror 151 at the time when the amplitude of light and darkness of the interference fringes becomes largest is the position where the optical path length of the measuring optical path 200 and the optical path length of the reference optical path 210 become equal to each other. By detecting the angle of rotation of the rotary mirror 151 by the rotary encoder 154 at that time, the reflecting position 210b in the direction of the optical axis is found. The optical path length of the reference optical path 210 is found from this reflecting position 210b.

In this case, since the rotary mirror is rotated at a constant angular speed, the optical path length of the reference optical path can be found without using the rotary encoder. For example, a certain rotation reference position of the rotary mirror 151 is determined (for example, an edge of the reflecting surface 151b is determined as the rotation reference position), and the optical path length of the reference optical path may be found from a period of time starting at the time when the edge moves across the reference optical path and ending at the time when the amplitude of light and darkness of the interference fringes becomes largest.

The reflecting position of the stationary mirror 152 is moved within a range indicated by broken lines of FIG. 1 by means of rotation of the rotary mirror 151. Therefore, the optical path length of the reference optical path can also be found by detecting this reflecting position using a means such as a line sensor.

That is, if a distance from the beam splitter 133 to a reference position (not shown) set in the measuring optical path 200 is made equal to a distance from the beam splitter 133 to a reflecting position 210c (edge) of the reflecting surface 151b of the rotary mirror 151, a distance from the reference position to the eye fundus 147 can be found as a distance from the reflecting position (edge) of the reflecting surface 151b of the rotary mirror 151 to the reflecting position 210b.

If the reference position of the measuring optical path 200 is made coincident to the reference position Y of the cornea distance measuring system 100, the intraocular length of the eye to be tested can be found by subtracting a distance $P_x$ from the reference position of the measuring optical path 200 to the cornea vertex 120P measured in the cornea distance measuring system 100 from the distance from the reference position to the eye fundus 147. These calculations are made by an arithmetic unit not shown.

As mentioned above, since the rotary mirror 151 can be rotated at an equal speed by the motor 154, the reflecting position 210b on the reflecting surface 151b of the rotary mirror 151 can be moved along the optical axis at an equal speed repeatedly. In other words, the optical path length of the reference optical path 210 can be varied at an equal speed repeated, and therefore the interference fringes can be generated repeatedly. Since the alignment and the diopter adjustment can be brought to optimum position while observing the interference fringes, the time for measurement can be shortened.

Furthermore, even if the eye to be tested is suffered from cataract, it can be known as to whether or not the interference fringes can be obtained simply by rotating the rotary mirror 151, and therefore an undue or wasteful measurement can be avoided and a measurable probability can be increased.

Moreover, since the alignment of the instrument and the diopter adjustment with respect to the eye to be tested can be carried out while observing the amplitude of the interference fringes, additional means for confirming the aligning condition and the diopter adjustment can be eliminated.

Furthermore, since the reflecting position 210b on the reflecting surface 151b of the rotary mirror 151 can be moved along the optical axis at an equal speed repeatedly, the frequency of light and darkness caused by the movement of the interference fringes observed by the photosensor 145 can be maintained constant, and this constant frequency can be detected as a signal with a high S/N through a band pass filter having a narrow band width. As a result, even an eye suffering from cataract where the amount of light reflecting from the eye fundus is small, can be measured.

Figure 9:
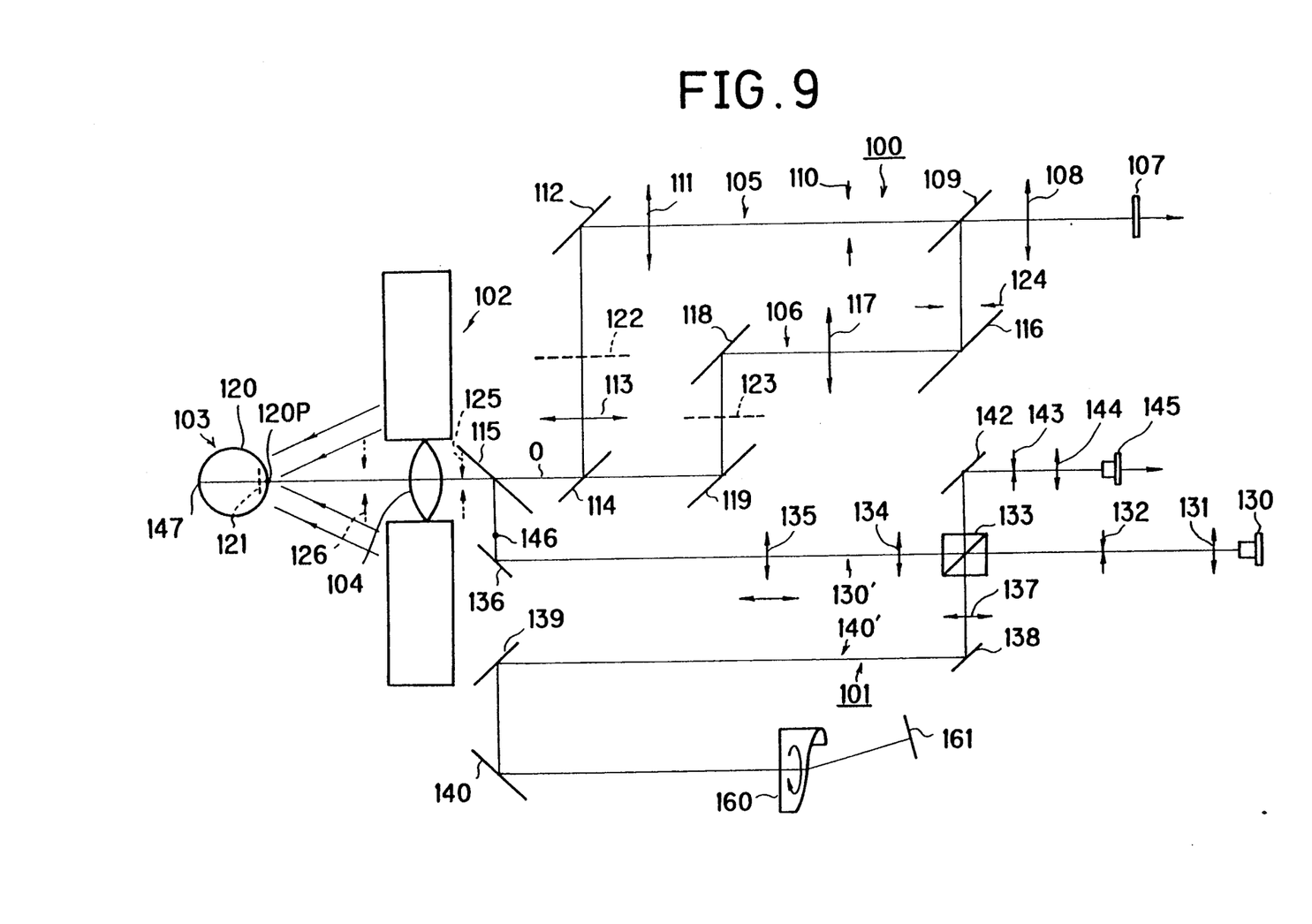
FIG. 9 is a view showing an arrangement of an optical system according to a second embodiment of the present invention.

FIG. 9 shows a second embodiment of the present invention. In this embodiment, since a circular wedge 160 is used instead of the rotary mirror 151, the optical path length can be varied by means of variation of the thickness of the circular wedge 160.

Figure 10:
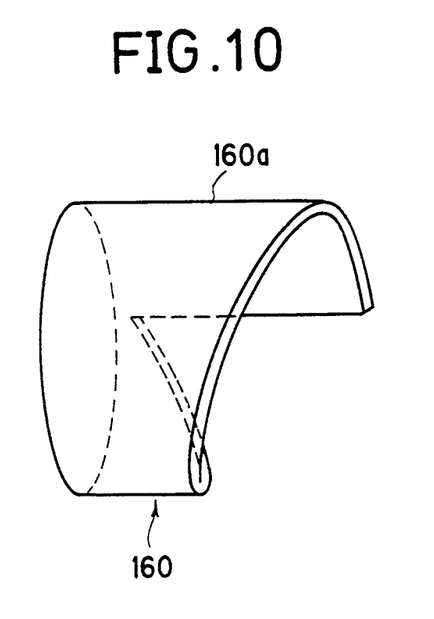
FIG. 10 is a perspective view showing a configuration of a circular wedge.

The numeral 161 denotes a stationary mirror which is positioned such that the reference light transmitted through the circular wedge 160 can be reflected correctly in the reverse way of the incident direction. As shown in FIG. 10, the circular wedge 160 is formed of a cylindrical optical member so that the thickness of the circular wedge 160 is continuously changed. The axial thickness of the cylindrical body 160a is varied into a linear shape with respect to the angle of rotation. A column like circular wedge may be used.

Owing to the above mentioned arrangement, when the circular wedge 160 is rotated at a constant angular speed, the optical path length is also varied at a constant speed. Thus, the circular wedge 160 exhibits the same effect as the rotary mirror 151. The variation of the optical path length is determined by a refractive index of the circular wedge 160 with respect to the wavelength of the light source, and the variation of the thickness. The larger the refractive index of the material used for the circular wedge is and the larger the variation of the thickness is, the larger the variation of the optical path length is.

The circular wedge 160 is rotated by a motor (not shown) as in the case of the rotary mirror 151. The angle of rotation is detected by a rotary encoder not shown.

Figure 11:
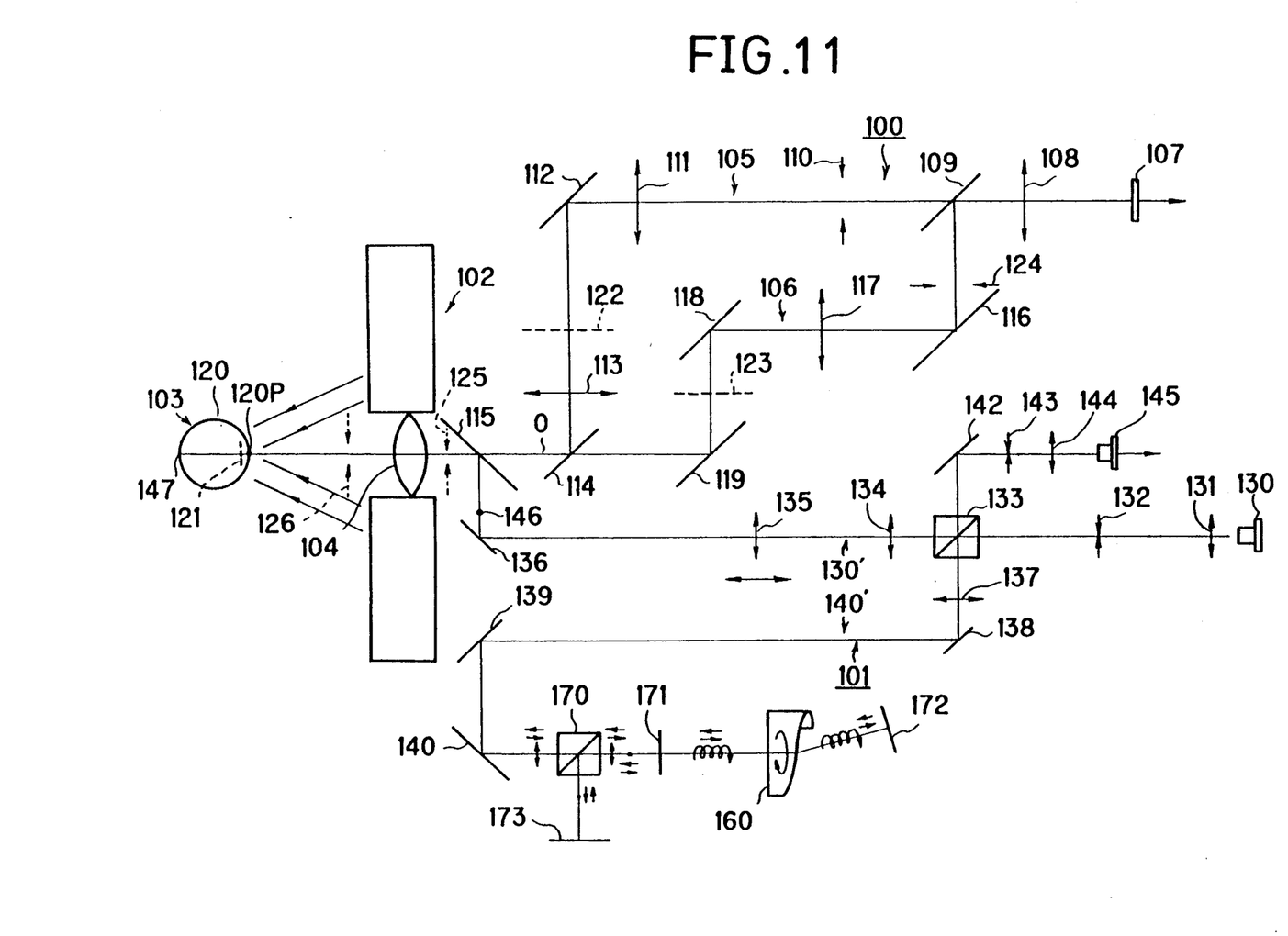
FIG. 11 is a view showing an arrangement of an optical system according to a third embodiment of the present invention.

FIG. 11 shows a third embodiment of the present invention. In this third embodiment, a polarized beam splitter 170, a quarter-wave plate ($\frac{1}{4}\lambda$ plate 171), and a stationary mirror 173 are added to the second embodiment ($\lambda$ is wavelength). The polarized beam splitter 170 permits only a component parallel to a sheet surface among various components contained in the reference light to transmit therethrough. Therefore, the transmitted light is made incident to the quarter-wave plate 171 as a circularly polarized light parallel to the sheet surface. When the linearly polarized light transmits through the quarter-wave plate, it is shifted in phase by 90 degrees, thus becoming a circularly polarized light. Such circularly polarized light is allowed to transmit through the circular wedge 160 and then reflected correctly in the reverse direction with respect to the coming direction by the stationary mirror 172. The circularly polarized light is allowed to transmit again through the circular wedge 160.

When the circularly polarized light transmits through the quarter-wave plate 171 next, it is shifted in phase again by 90 degrees. As a result, the shifted light is made incident to the polarized beam splitter 170 as a linearly polarized light vertical to the sheet surface. The linearly polarized light vertical to the sheet surface is reflected toward the stationary mirror 173 by the polarized beam splitter 170. The linearly polarized reference light reflected by the stationary mirror 173 is reflected correctly in the reverse direction with respect to the coming direction. This reference light is reflected again by the polarized beam splitter 170, transmitted through the polarized beam splitter 170 now as a linearly polarized light parallel to the sheet surface via the quarter-wave plate 171, the circular wedge 160, the stationary mirror 172, the circular wedge 160, and the quarter-wave plate 171, and then guided to the photosensor 145. In this embodiment, since the reference light is allowed to transmit through the circular wedge 160 four times (double reciprocation) in a midway of the reference optical path, there can be obtained the advantage in that the optical path can be varied twice as large as the second embodiment.

Figure 12:
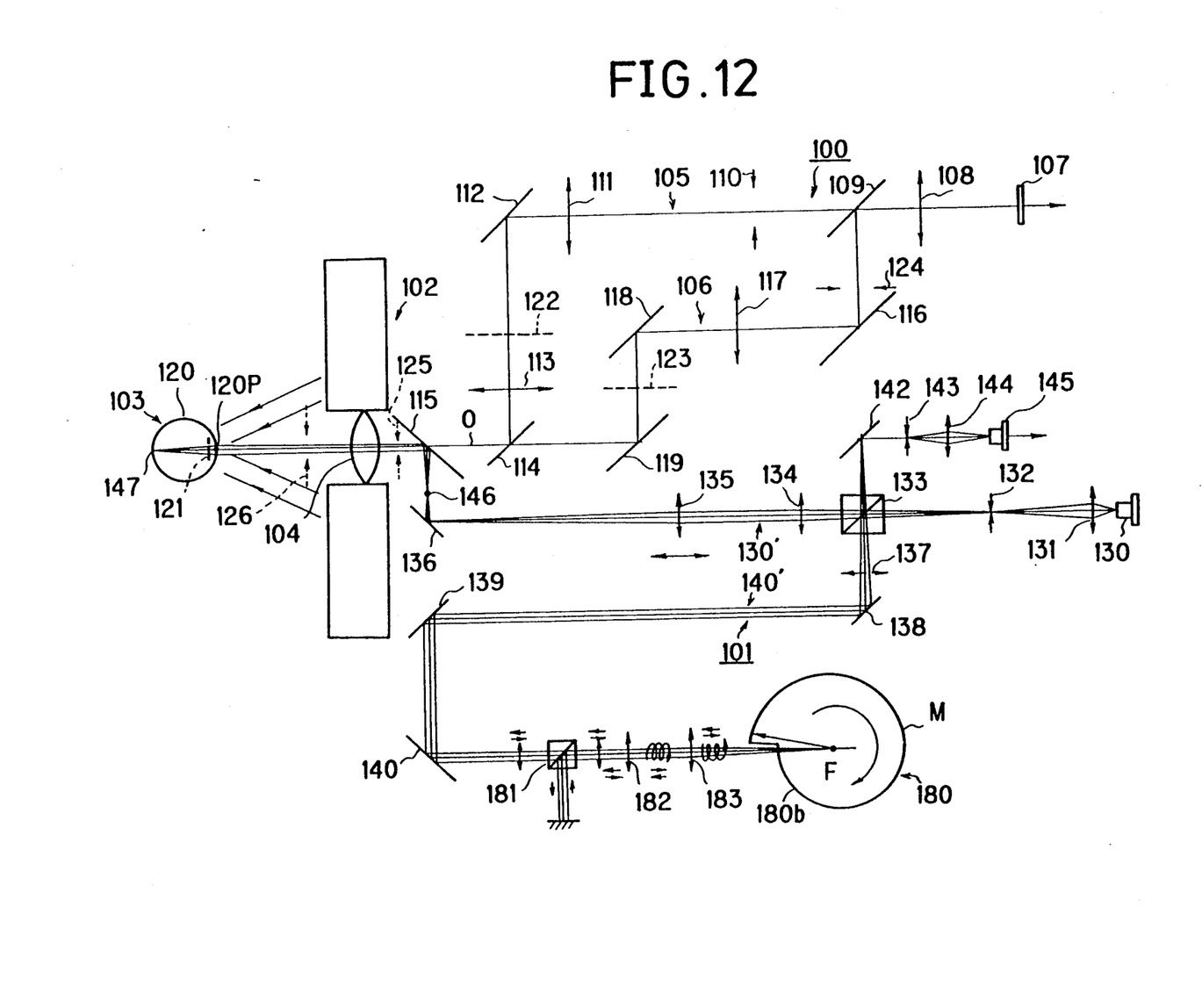
FIG. 12 is a view showing an arrangement of an optical system according to a fourth embodiment of the present invention.

FIG. 12 shows a fourth embodiment of the present invention. In this embodiment, a spiral mirror 180 is used instead of the rotary mirror 151.

Figure 13:
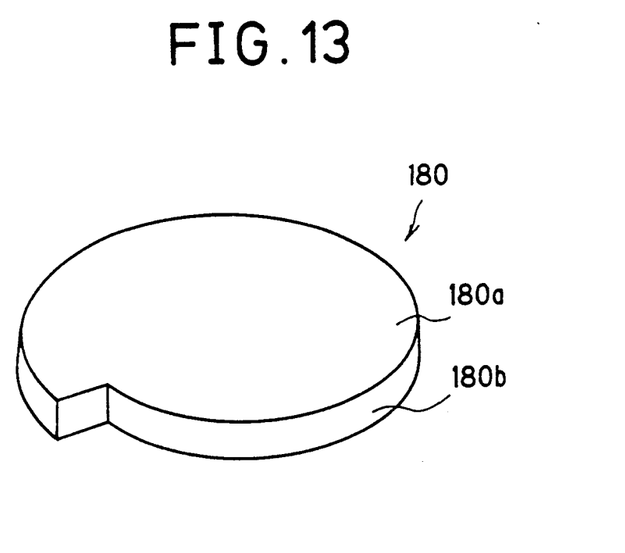
FIG. 13 is a perspective view showing a configuration of a spiral mirror.

As shown in FIG. 13, the spiral mirror 180 is formed of a disc-like body 180a having a predetermined thickness. A reflecting surface 180b is formed on a peripheral surface of the disc-like body 180a. The reflecting surface 180b is arranged such that a tangential line thereof normally forms a constant angle. In this case, although the reference optical path length is not varied at a constant speed, there can still be obtained the similar effect as in the other embodiments because the percentage of the variation is small.

The functions of a polarized beam splitter 181 and a quarter-wave plate 182 shown in FIG. 12 is the same as the third embodiment.

The reference light transmitted through both the polarized beam splitter 181 and the quarter-wave plate 182 is made incident to the spiral mirror 180 while being converged in a direction horizontal to the sheet surface owing to the function of a cylindrical lens 183, and reflected by a reflecting surface of the spiral mirror 180 so as to be returned in the reverse way with respect to the incident direction. At that time, in order to effectively return the reflected light, it is necessary for the spiral mirror 180 to be arranged such that the optical axis of the reference light is perpendicular to the reflecting surface 180b and also for the cylindrical lens 183 such that a focal point F thereof is located at the center of curvature of the reflecting surface 180b of the spiral mirror 180. However, since the curvature of the reflecting surface 180b of the spiral mirror 180 is not constant actually, it is practically impossible to satisfy this condition.

However, by setting a focal length of the cylindrical lens 183 to be long enough to the beam diameter of the reference light and by setting the curvature of the reflecting surface of the spiral mirror 180 to be large enough to the amount of variation of the radius of the spiral mirror 180, the reflection light can be efficiently returned.

In this embodiment, both the polarized beam splitter 181 and the quarter-wave plate 182 are used. However, the polarized beam splitter 181 and the quarter-wave plate 182 may be eliminated. In that case, the variation of the optical path length is reduced to one-half but this is still satisfactory in view of function.

The spiral mirror 180 is rotated by a motor not shown.

The angle of rotation is detected by a rotary encoder not shown.

The present invention is not limited to the above embodiments, and various modifications can be made without departing from the scope of the appended claims.

What is claimed is:

1. An intraocular length measuring instrument including:
   a light source having a short coherent length;
   a beam splitter for forming a measuring optical path via the interior of an eye to be tested and a reference optical path within said instrument, and guiding a beam of light from said light source to both said measuring optical path and said reference optical path;
   a first light receiving means for interfering light reflected by an intraocular object to be measured after passing along said measuring optical path with light coming through said reference optical path and receiving a resultant interference light;
   an intraocular object position measuring means for finding an optical path difference from the reference optical path and the measuring optical path according to a peak position of a signal coming from said first light receiving means and an optical path length of the reference optical path;

a light irradiating optical means for irradiating a light beam to the cornea of said eye to be tested;

a light receiving optical means for introducing a reflected light from said cornea to a second light receiving means; and a corneal position measuring means for finding a position of said cornea from an output of said second light receiving means;

a rotatable optical path length variable means for varying the optical path length of the reference optical path in accordance with an angle of rotation; and a rotary means for rotating the optical path length variable means to vary the optical path length of the reference optical path sequentially.

2. In an intraocular length measuring instrument in which a beam of light is split into two beams of light, one of said split beams of light is guided, as a reference beam of light, to an optical path length variable optical means disposed in a reference optical path and adapted to vary an optical path length of said reference optical path, and the other of said split beams of light is guided, as a measuring beam of light, to an intraocular object to be measured, a reference reflection light from said optical path length variable optical member and a measuring reflection light from said intraocular object to be measured being interfered with each other to obtain an interference signal, thereby finding a position of said intraocular object to be measured, the improvement being characterized in that said optical path length variable optical means comprises a rotary optical member and a stationary mirror, a rotary axis of said rotary optical means being in parallel or vertical to an optical axis of said reference optical path.

3. An intraocular length measuring instrument according to claim 2, wherein said rotary optical means is formed of a cylindrical or disc-like rotary mirror, and an end face of said rotary optical means is defined as a spiral reflecting surface.

4. An intraocular length measuring instrument according to claim 3, wherein said stationary mirror is a phase conjugate mirror.

5. An intraocular length measuring instrument according to claim 3, wherein an angle of rotation of said cylindrical or disc-like mirror and the optical path length are in linear relation in variation.

6. An intraocular length measuring instrument according to claim 5, wherein the optical path length of said reference optical path is calculated mathematically based on variation of a reflecting position on said stationary mirror of said reference light which is made incident to said stationary mirror.

7. An intraocular length measuring instrument according to claim 2, wherein said rotary optical means is formed of a cylindrical or column-like circular wedge, and an optical path of said reference optical path is parallel to a rotary axis of said circular wedge, at least one end face of said rotary optical means being defined as a spiral-shaped transmission surface.

8. An intraocular length measuring instrument according to claim 7, wherein an angle of rotation of said circular wedge and a variation of said optical path are in linear relation, and a a thickness of the circular wedge is varied.

9. An intraocular length measuring instrument according to claim 7, wherein a polarized beam splitter and a quarter wave plate are placed in said reference optical path, and said reference light transmits through said circular wedge four times.

10. An intraocular length measuring instrument according to claim 2, wherein said optical path length variable optical means is formed of a disk-like spiral mirror, and formed on a peripheral surface thereof with a spiral reflecting surface, a rotary axis of said spiral mirror is intersected at right angles with the optical axis.

* * * * *

UNITED STATES PATENT AND TRADEMARK OFFICE
CERTIFICATE OF CORRECTION

PATENT NO. : 5,329,321
DATED : July 12, 1994
INVENTOR(S) : Hiroshi KOIZUMI

It is certified that error appears in the above-indentified patent and that said Letters Patent is hereby corrected as shown below:

Claim 8, Column 14, Line 27 delete "a" (Second Occurrence).

Signed and Sealed this

Twenty-fifth Day of April, 1995

Attest:

BRUCE LEHMAN

Attesting Officer     Commissioner of Patents and Trademarks